US00PP23597P2

(12) United States Plant Patent
Fischer-Toehl

(10) Patent No.: US PP23,597 P2
(45) Date of Patent: May 14, 2013

(54) GERANIUM PLANT NAMED 'SIL BALDO 448'

(50) Latin Name: *Pelargonium×hortorum*
Varietal Denomination: Sil Baldo 448

(75) Inventor: Ilse Fischer-Toehl, Kirchlinteln (DE)

(73) Assignee: Ball Horticultural Company, West Chicago, IL (US)

( * ) Notice: Subject to any disclaimer, the term of this patent is extended or adjusted under 35 U.S.C. 154(b) by 447 days.

(21) Appl. No.: 12/924,664

(22) Filed: Oct. 1, 2010

(51) Int. Cl.
*A01H 5/00* (2006.01)

(52) U.S. Cl.
USPC ..... Plt./325

(58) Field of Classification Search ..... Plt./325
See application file for complete search history.

*Primary Examiner* — June Hwu
*Assistant Examiner* — Louanne Krawczewicz Myers
(74) *Attorney, Agent, or Firm* — Audrey Charles

(57) ABSTRACT

A new and distinct cultivar of Geranium plant named 'Sil Baldo 448', characterized by its semi-double type, fuchsia and cherry-red bicolored flowers, dark green-colored foliage, low to moderate vigor, and compact, upright growth habit growth habit, is disclosed.

1 Drawing Sheet

Latin name of genus and species of plant claimed: *Pelargonium×hortorum.*
Variety denomination: 'Sil Baldo 448'.

BACKGROUND OF THE INVENTION

The present invention relates to a new and distinct cultivar of Geranium plant botanically known as *Pelargonium×hortorum* and hereinafter referred to by the cultivar name 'Sil Baldo 448'.

The new cultivar originated in a controlled breeding program in Weener, Germany, California during June through December 2004. The objective of the breeding program was the development of Geranium cultivars that flower uniformly and have large flowers, dark green-colored foliage, and a moderately vigorous, upright growth habit.

The new Geranium cultivar is the result of cross-pollination. The female (seed) parent of the new cultivar is 'SEL Lucky', not patented, characterized by its double-type, bluish red to purple colored flowers, dark green-colored foliage, and moderately vigorous, upright growth habit. The male (pollen) parent of the new cultivar is the proprietary *Pelargonium×hortorum* breeding selection designated E 065, not patented, characterized by its single-type, fuchsia and cherry-red bicolored flowers, dark green-colored foliage, low vigor, and compact, upright growth habit. The new cultivar was discovered and selected as a single flowering plant within the progeny of the above stated cross-pollination during June through August 2005 in a controlled environment at Weener, Germany.

Asexual reproduction of the new cultivar by terminal stem cuttings since August 2005 at Weener, Germany, Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Sil Baldo 448' as a new and distinct cultivar of Geranium plant:

1. Semi-double type, fuchsia and cherry-red bicolored flowers;
2. Dark green-colored foliage;
3. Low to moderate vigor; and
4. Compact, upright growth habit.

Plants of the new cultivar differ from plants of the female parent primarily in flower type and growth vigor and from plants of the male parent primarily in flower type and growth vigor. The new cultivar is slightly more vigorous than the male parent.

Of the many commercially available Geranium cultivars, the most similar in comparison to the new cultivar is Designer Light Pink Sizzle 'Baldeslipzle', U.S. Plant Pat. No. 18,863. However, in side by side comparisons, plants of the new cultivar differ from plants of 'Baldeslipzle' in at least the following characteristics:

1. Plants of the new cultivar have a darker flower color than plants of 'Baldeslipzle'; and
2. Plants of the new cultivar have a darker foliage color than plants of 'Baldeslipzle'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Sil Baldo 448'. The plants were grown in 4-inch pots for 7 weeks in a greenhouse at West Chicago, Ill.

DETAILED BOTANICAL DESCRIPTION

Figure 1:
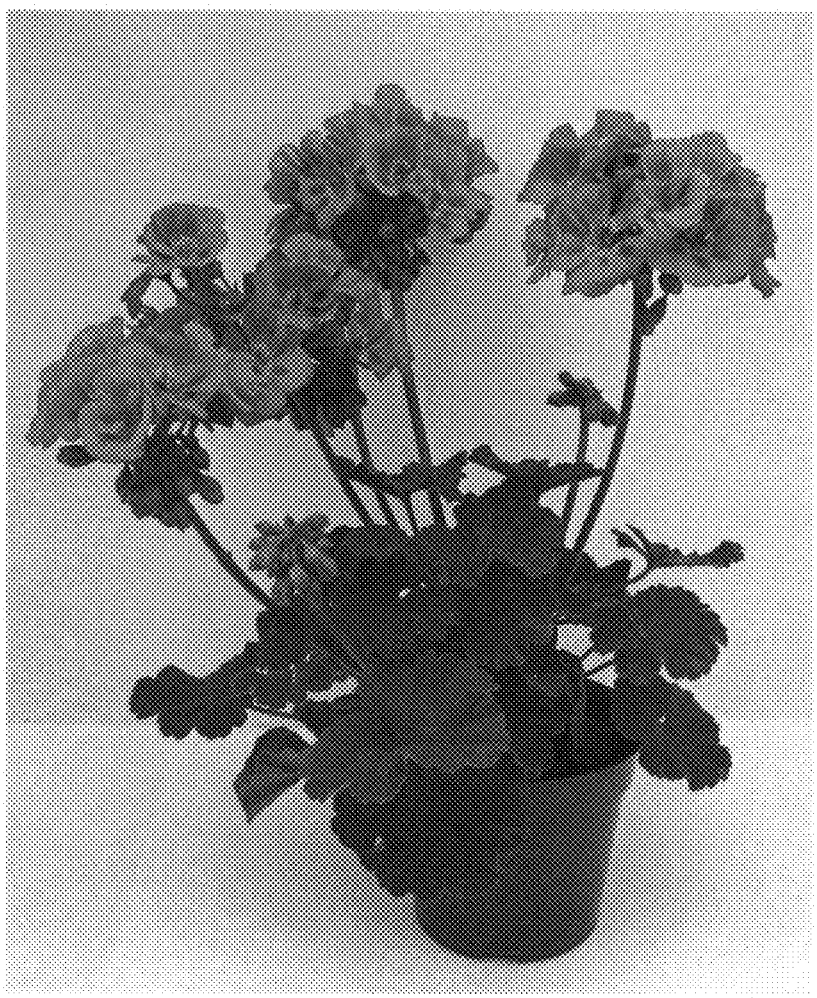
FIG. 1 illustrates a side view of the overall growth and flowering habit of 'Sil Baldo 448'.
Figure 2:
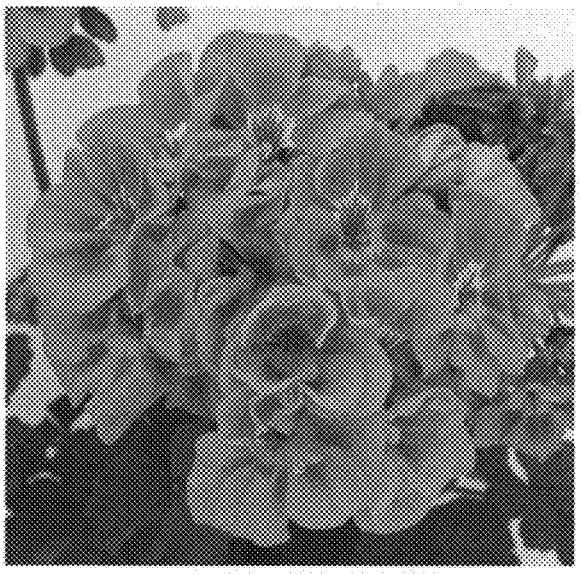
FIG. 2 illustrates a close-up view of an individual umbel of 'Sil Baldo 448'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined in August 2010 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4-inch pots for 7 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Pelargonium×hortorum* cultivar Sil Baldo 448.

Parentage:

*Female parent*.—'SEL Lucky', not patented.

*Male parent*.—Proprietary *Pelargonium×hortorum* breeding selection designated E 065, not patented.

Propagation:

*Type cutting*.—Terminal stem.

*Time to initiate roots*.—Approximately 10 to 14 days.

*Time to produce a rooted cutting*.—Approximately 21 to 28 days.

*Root description*.—Fibrous.

*Rooting habit*.—Freely branching.

Plant description:

*Commercial crop time*.—Approximately 8 to 9 weeks from a rooted cutting to finish in a 10 cm pot.

*Growth habit and general appearance*.—Low to moderate vigor, compact, upright.

*Size*.—Height from soil level to top of plant plane (to top of umbels): Approximately 19.8 cm. Height from soil level to top of foliage: Approximately 10.0 cm. Width: Approximately 28.2 cm.

*Branching habit*.—Freely basal branching, pinching enhances basal branching. Quantity of main branches per plant: Approximately 3.

*Branch*.—Strength: Strong. Length: Approximately 4.3 cm. Diameter: Approximately 5.0 mm. Length of central internode: Approximately 9.0 mm. Texture: Densely pubescent with a mixture of glandular and nonglandular hairs. Gland color: Colorless, transparent. Color of young and mature stems: 144A.

Foliage description:

*General description*.—Quantity of leaves per lateral branch: Approximately 7. Fragrance: Slight. Form: Simple. Arrangement: Opposite.

*Leaves*.—Aspect: Petiole is at an acute angle to stem, blade is perpendicular to stem. Shape: Reniform. Margin:Bicrenate. Apex: Obtuse. Base: Cordate. Venation pattern: Palmate. Length of mature leaf: Approximately 6.6 cm. Width of mature leaf: Approximately 7.6 cm. Texture of upper and lower surfaces: Densely pubescent with a mixture of glandular and nonglandular hairs. Gland color: Colorless, transparent. Color of upper surface of young and mature foliage: Darker than 137A with venation of 144A to indistinguishable. Color of lower surface of young and mature foliage: Closest to 138A with venation of 145A. Zonation pattern: Not discernible.

*Petiole*.—Length: Approximately 5.4 cm. Diameter: Approximately 2.0 mm. Texture: Densely pubescent with a mixture of glandular and nonglandular hairs. Gland color: Colorless, transparent. Color: 144A.

Flowering description:

*Flowering habit*.—'Sil Baldo 448' is freely flowering under outdoor growing conditions with substantially continuous blooming from spring through autumn and year-round in greenhouse environment.

*Lastingness of individual flower on the plant*.—Approximately 5 to 7 days.

Inflorescence description:

*General description*.—Type: Umbel. Positioned above foliage. Quantity of fully open umbels per plant: Approximately 2. Quantity of developing umbels per plant: Approximately: 4. Fragrance: None. Length or height: Approximately 5.5 cm. Width: Approximately 9.5 cm. Quantity of fully open flowers per inflorescence: Approximately 21.

*Peduncle*.—Strength: Strong. Aspect: Erect. Length: Approximately 12.0 cm. Diameter: Approximately 4.0 mm. Texture: Densely pubescent with a mixture of glandular and nonglandular hairs. Gland color: Colorless, transparent. Color: 144A.

Flower description:

*General description*.—Type: Semi-double.

*Bud*.—Rate of opening: Generally takes 3 to 5 days for bud to progress from first color to fully open flower.

*Bud just before opening*.—Shape: Elliptic. Length: Approximately 1.5 cm. Width: Approximately 7.0 mm. Sepal texture: Densely pubescent with a mixture of glandular and nonglandular hairs. Gland color: 29A and colorless, transparent. Petal texture: Glabrous. Petal color: N74C to N74A.

*Corolla*.—Shape: Round. Diameter: Approximately 4.4 cm. Depth: Approximately 2.0 cm.

*Petals*.—Quantity: Approximately 5 to 7 petals and 0 to 2 irregularly-shaped petaloids per flower. Shape: Obovate. Appearance: Iridescent. Margin: Entire. Apex: Obtuse. Base: Attenuate. Length of upper petals: Approximately 2.6 cm. Width of upper petals: Approximately 2.2 cm. Length of lower petals: Approximately 2.3 cm. Width of lower petals: Approximately 2.1 cm. Texture of upper and lower surfaces: Glabrous. Color of upper surface of upper petals when fully open: N74A with a central spot of N66A; base of pure white, purer white than RHS 155D with venation of N66A. Color of lower surface of upper and lower petals when fully open: N66C with venation of N66A. Color of upper surface of lower petals when fully open: N74A with a central spot of N66A.

*Calyx*.—Shape: 5-pointed star. Diameter: Approximately 2.0 cm.

*Sepals*.—Quantity per flower: Approximately 5, fused at base. Shape: Lanceolate. Margin: Entire. Apex: Acuminate. Length of upper sepal: Approximately 1.2 cm. Width of upper sepal: Approximately 4.0 mm. Length of lower sepals: Approximately 1.2 cm. Width of lower sepals: Approximately 3.0 mm. Texture of upper surface: Glabrous. Texture of lower surface:

Densely pubescent with a mixture of glandular and nonglandular hairs. Gland color: 29A and colorless, transparent. Color of upper and lower surfaces: 144A with and overlay of 187B.

*Pedicel*.—Strength: Strong. Aspect: Acute angle to peduncle. Length: Approximately 2.6 cm. Diameter: Approximately 2.0 mm. Texture: Densely glandular pubescent. Gland color: 29A and colorless, transparent. Color: 144A with a heavy overlay of 187B.

*Reproductive organs*.—Androecium: Quantity of mature stamens: Approximately 5 per flower. Anther shape: Oblong. Anther length: Approximately 2.0 mm. Anther color: 61A. Filament length: Approximately 8.0 mm. Filament color: Pure white with an overlay of 61C nearest the anther. Pollen amount: Moderate. Pollen color: 32A. Gynoecium: Pistil quantity: 1 per flower. Pistil length: Approximately 1.2 cm. Stigma shape: 5 branched. Stigma length: Approximately 3.0 mm. Stigma color: 61A. Style length: Approximately 3.0 mm. Style color: 61B. Ovary length: Approximately 6.0 mm. Ovary texture: Densely pubescent. Ovary color: 145B.

Seed and fruit production: Neither seed nor fruit production has been observed.

Disease and pest resistance: Resistance to pathogens and pests common to Geranium has not been observed.

What is claimed is:

1. A new and distinct cultivar of Geranium plant named 'Sil Baldo 448', substantially as herein shown and described.

* * * * *